United States Patent
Longoria

(10) Patent No.: US 9,554,907 B2
(45) Date of Patent: Jan. 31, 2017

(54) SYNTHETIC CHORD

(71) Applicant: LC Therapeutics, Inc., Fremont, CA (US)

(72) Inventor: James Longoria, Sacramento, CA (US)

(73) Assignee: LC Therapeutics, Inc., Sacramento, CA (US)

( * ) Notice: Subject to any disclaimer, the term of this patent is extended or adjusted under 35 U.S.C. 154(b) by 517 days.

(21) Appl. No.: 13/895,015

(22) Filed: May 15, 2013

(65) Prior Publication Data

US 2014/0155989 A1    Jun. 5, 2014

Related U.S. Application Data

(63) Continuation of application No. 12/353,898, filed on Jan. 14, 2009.

(51) Int. Cl.
*A61F 2/24* (2006.01)
*A61B 17/04* (2006.01)
(Continued)

(52) U.S. Cl.
CPC .......... *A61F 2/2463* (2013.01); *A61B 17/0401* (2013.01); *A61F 2/2457* (2013.01);
(Continued)

(58) Field of Classification Search
CPC ............ A61B 17/0401; A61B 17/0406; A61B 2017/00243; A61B 2017/00783; A61B 2017/00862; A61B 2017/00867; A61B 2017/0427; A61B 2017/048; A61B 2017/06057; A61B 2017/0419; A61F 2/2457; A61F 2/2454
See application file for complete search history.

(56) References Cited

U.S. PATENT DOCUMENTS 5,002,563 A    3/1991  Pyka et al.
5,269,783 A   12/1993  Sander
(Continued)

FOREIGN PATENT DOCUMENTS

WO   WO 02/30295 A1      4/2002
WO   WO2004112658 A1    12/2004
(Continued)

OTHER PUBLICATIONS

Bizzarri et al., "Different ways to repair the mitral valve with artificial chordae: a systematic review", Journal of Cardiothoracic Surgery, vol. 5, No. 22, pp. 1-6 (2010).
(Continued)

*Primary Examiner* — Alexander Orkin
(74) *Attorney, Agent, or Firm* — Bret E. Field; Bozicevic, Field & Francis LLP

(57) ABSTRACT

Synthetic chord devices and methods for using the same for connecting tissues are provided. Aspects of the synthetic chord device include a flexible cord having an attachment element at both a first and a second end, wherein each attachment element includes a piercing member coupled to a securing member that attaches the flexible cord to a first tissue. At least a portion of the flexible cord can be configured to be secured to a second tissue. Aspects of the invention also include sets of the synthetic chord device with pre-measured flexible cords. The devices and methods of the invention find use in a variety of applications, such as in is applications in which it is desired to repair a heart valve.

8 Claims, 7 Drawing Sheets

(51) Int. Cl.
*A61B 17/06* (2006.01)
*A61B 17/00* (2006.01)

(52) U.S. Cl.
CPC .......... *A61B 17/06166* (2013.01); *A61B 2017/00243* (2013.01); *A61B 2017/00783* (2013.01); *A61B 2017/00862* (2013.01); *A61B 2017/00867* (2013.01); *A61B 2017/048* (2013.01); *A61B 2017/0427* (2013.01); *A61B 2017/06057* (2013.01); *A61F 2250/0064* (2013.01)

(56) References Cited

U.S. PATENT DOCUMENTS

| | | | |
|---|---|---|---|
| 5,383,904 | A | 1/1995 | Totakura et al. |
| 5,500,000 | A | 3/1996 | Feagin et al. |
| 5,593,424 | A | 1/1997 | Northrup, III |
| 5,709,695 | A | 1/1998 | Northrup, III |
| 6,029,806 | A | 2/2000 | Cerwin et al. |
| 6,231,561 | B1 | 5/2001 | Frazier et al. |
| 6,358,277 | B1 | 3/2002 | Duran |
| 6,506,197 | B1* | 1/2003 | Rollero et al. ............ 606/148 |
| 6,514,265 | B2 | 2/2003 | Ho et al. |
| 6,607,541 | B1 | 8/2003 | Gardiner |
| 6,613,059 | B2 | 9/2003 | Schaller et al. |
| 6,641,593 | B1 | 11/2003 | Schaller et al. |
| 6,797,002 | B2 | 9/2004 | Spence et al. |
| 6,913,607 | B2 | 7/2005 | Ainsworth et al. |
| 6,964,684 | B2 | 11/2005 | Ortiz et al. |
| 7,066,954 | B2 | 6/2006 | Ryan et al. |
| 7,963,973 | B2 | 6/2011 | Nguyen et al. |
| 8,147,542 | B2 | 4/2012 | Maisano et al. |
| 8,252,050 | B2 | 8/2012 | Maisano et al. |
| 2001/0018592 | A1 | 8/2001 | Schaller et al. |
| 2001/0041916 | A1 | 11/2001 | Bonutti |
| 2002/0029080 | A1 | 3/2002 | Mortier et al. |
| 2002/0165561 | A1 | 11/2002 | Ainsworth et al. |
| 2003/0105519 | A1* | 6/2003 | Fasol et al. ............ 623/2.1 |
| 2003/0149447 | A1* | 8/2003 | Morency et al. ............ 606/228 |
| 2003/0171641 | A1 | 9/2003 | Schweich, Jr. et al. |
| 2004/0039392 | A1 | 2/2004 | Trieu |
| 2004/0111099 | A1 | 6/2004 | Nguyen et al. |
| 2005/0159810 | A1 | 7/2005 | Filsoufi |
| 2005/0192630 | A1 | 9/2005 | Maas et al. |
| 2006/0030885 | A1 | 2/2006 | Hyde |
| 2006/0205995 | A1 | 9/2006 | Browning |
| 2007/0038249 | A1 | 2/2007 | Kolster |
| 2007/0066863 | A1 | 3/2007 | Rafiee et al. |
| 2007/0118213 | A1 | 5/2007 | Loulmet |
| 2007/0173930 | A1 | 7/2007 | Sogard et al. |
| 2007/0173932 | A1 | 7/2007 | Cali et al. |
| 2007/0208377 | A1 | 9/2007 | Kaplan et al. |
| 2008/0051807 | A1 | 2/2008 | St. Goar et al. |
| 2009/0082806 | A1 | 3/2009 | West, Jr. et al. |
| 2009/0177274 | A1 | 7/2009 | Scorsin et al. |
| 2009/0248067 | A1* | 10/2009 | Maiorino ............ 606/228 |
| 2009/0312791 | A1 | 12/2009 | Lindh, Sr. et al. |
| 2010/0121435 | A1 | 5/2010 | Subramanian et al. |
| 2010/0161042 | A1 | 6/2010 | Maisano et al. |
| 2010/0179574 | A1 | 7/2010 | Longoria et al. |
| 2010/0280603 | A1 | 11/2010 | Maisano et al. |
| 2010/0280604 | A1 | 11/2010 | Zipory et al. |
| 2010/0280605 | A1 | 11/2010 | Hammer et al. |
| 2010/0298929 | A1 | 11/2010 | Thornton et al. |
| 2012/0078355 | A1 | 3/2012 | Zipory et al. |
| 2012/0136436 | A1 | 5/2012 | Cabiri et al. |

FOREIGN PATENT DOCUMENTS

| | | |
|---|---|---|
| WO | WO 2010/073246 A2 | 7/2010 |
| WO | WO 2010/128502 A1 | 11/2010 |
| WO | WO 2010/128503 A2 | 11/2010 |

OTHER PUBLICATIONS

Chiappini et al., "Replacement of chordae tendineae with polytetrafluoroethylene (PTFE) sutures in mitral valve repair : early and long-term results", J Heart Valve Dis. Sep. 2006; 15(5): 657-663 Abstract.

Cook et al., "Significant reduction in annuloplasty operative lime with the use of nitinol clips in robotically assisted mitral valve repai"; J. Thorac Cardiovasc. Surg. May 2007; 133(5): 12,64-67.

Duran et al., "Techniques for ensuring hte correct length of new mitral chords"; J Heart Valve Disease Mar. 2003; 12(2): 156-161.

Gillinov et al., "Pre-Measured Artificial Chordae for MV Repair"; Annals of Thoracic Surgery Aug. 2007; 84: 2127-2129.

Kuntz et al., "Early and mid-term results of mitral valve repair using premeasured Gore-Tex loops ('loop technique')"; Eur J Cariothorac Surg. Apr. 2008; 33(4): 566-572; Epub Feb. 12, 2008.

Maisano et al., "Beating-heart implantation of adjustable length mitral valve chordae: acute and chronic experience in an animal model", European Journal of Cardio-thoracic Surgery, vol. 40, No. 4, pp. 840-847 (2011).

Maisano et al., "Neochordae Implantation Made Easy With an Adjustable Device", Innovations, vol. 5, No. 4, pp. 287-290 (2010).

Maselli et al., "A New Method for artificial chordae length "tuning" in mitral valve repair: Preliminary Experience"; J. Thorac Cardiovas. Surgery Aug. 2007; 134: 454-459.

Smith et al., "Endoscopic placement of multiple artificial chordae with robotic assistance and nitinol clip fixation", J. Thorac Cardiovasc. Surgery Mar. 2008; 135(3): 610-614.

Tomita et al., "Surgical application for a prolapse of the anterior mitral leaflet by replacing artificial chordae with polytetraflouroethylene grafts"; Surg. Today; (2005) 35(10): 81 2-8 Abstract.

Zussa et al., "Artificial chordae in the treatment of anterior mitral leaflet pathology"; Cardiovasc. Surgery Feb. 1997; 5(1) : 125-128 Abstract.

* cited by examiner

SYNTHETIC CHORD

INTRODUCTION

The mitral valve is composed of two leaflets attached to the mitral valve annulus, which are supported at the free edge by chordae tendinae (chords) attached to the inside wall of the left ventricle and to the papillary muscles. However, sometimes one or both of the valve leaflets become loose, due to loosening or failure of one or more of these chords. The valve then prolapses, and the seal that it normally provides between the left atrium and left ventricle becomes compromised, causing the blood to flow back into the left atrium during systole.

A variety of methods have been described for placement of artificial chordae tendineae to correct mitral valve leaflet prolapse and treat diseased mitral valve chordae tendineae. However, there are many technical challenges in this surgical is procedure, especially when performed with minimally invasive techniques. The most common method of repairing the valves is to create synthetic chordae tendineae from polytetrafluoroethylene (PFTE), which are sutured into place between the papillary muscle of the heart wall and the mitral valve leaflets. Cardiac surgeons usually are required to perform the time-consuming process of measuring and cutting the necessary length of synthetic chordae tendineae material during the surgical procedure after they have measured the dimensions of the patient's heart valves. In addition, anchoring the synthetic chordae tendineae in the papillary muscle and securing the sutures through the leaflets is often technically difficult in minimally invasive procedures, because of limitations in using 2-dimensional video for viewing the surgical field, limited exposure of the surgical field, and limited degrees of freedom using standard thoracoscopic instrumentation.

Therefore, there is considerable interest in the development of new techniques for use in both open and minimally invasive procedures that address the problems of accurately and efficiently securing the valve leaflets during cardiac surgery.

SUMMARY

Synthetic chord devices and methods for using the same for connecting tissues are provided. Aspects of the synthetic chord devices of the invention include a flexible cord having attachment elements at both a first and second end, wherein each attachment element includes a piercing member coupled to a securing member, where the securing member attaches the flexible cord to a first tissue. At least a portion of the flexible cord is configured to be secured to a second tissue. Aspects of the invention also include sets of the synthetic chord devices, e.g., of different sizes. The devices and methods of the invention find use in a variety of applications, such as in applications in which it is desired to repair a heart valve.

DETAILED DESCRIPTION

Figure 1A:
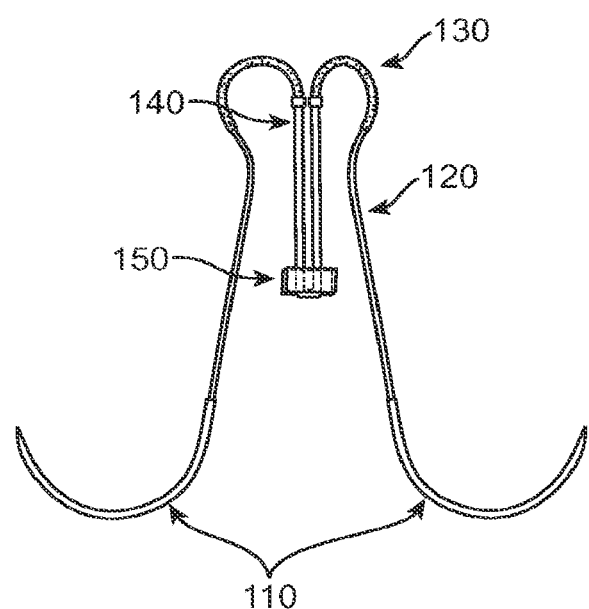
FIGS. 1A and B provide a view of the device in accordance with an embodiment of the invention.

Synthetic chord devices and methods for using the same for connecting tissues are provided. Aspects of the synthetic chord devices include a flexible cord having an attachment element at both a first and a second end, wherein each attachment element includes a piercing member coupled to a securing member that attaches the flexible cord to a first tissue. At least a portion of the flexible cord is configured to be secured to a second tissue. Aspects of the invention also include sets of the synthetic chord devices, e.g., of different sizes. The devices and methods of the invention find use in a variety of applications, such as in applications in which it is desired to repair a heart valve.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual is publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Devices

Synthetic chord devices according to certain embodiments of the invention are devices that are configured to connect or align tissues, or connect tissue and a prosthesis, or a combination thereof. The subject devices and methods can be used in endovascular, minimally invasive surgical, open surgical, or other interventional procedures. As such, devices of the invention can be configured to secure a valve leaflet, such as a mitral valve leaflet or tricuspid valve leaflet, to a papillary muscle.

Embodiments of the synthetic chord device include a flexible cord having an attachment element at both a first and a second end, wherein each attachment element includes a piercing member coupled to a securing member that attaches the flexible cord to a first tissue. At least a portion of the flexible cord can be configured to be secured to a second tissue.

A synthetic chord device of the subject invention is a synthetic, or artificial, flexible cord which has attachment elements at both ends of the cord, for attaching the cord to a tissue. In some embodiments, the flexible cord is configured to be is attached to a prosthesis, or to a device that substitutes for or supplements a missing or defective part of the body, e.g., a synthetic cardiac valve, or a porcine valve. In some embodiments, a synthetic chord device is configured to be used as a synthetic chorda tendinea for use in repair of a cardiac valve, e.g., the mitral valve.

The flexible cord element of the subject invention is a flexible elongated structure having a first end and a second end, constructed of a material suitable for use in the body that can be used in the methods of the subject invention, e.g., attaching a valve leaflet to the underlying cardiac tissue. The flexible cord element has a length suitable for extending from a first tissue to a second tissue and back to a first tissue, such that the flexible cord provides two segments, each segment secured to both the first and the second tissue. For example, in certain embodiments, each segment of the flexible cord would be equal to half of the total length of the flexible cord. In some embodiments, the flexible cord element has a length suitable for extending from a first tissue (e.g., a mitral valve leaflet) to where it is secured to a second tissue (e.g., a papillary muscle) and back to the first tissue. In this embodiment the length of the flexible cord may range from 8 mm to 60 mm, such as from 16 mm to 48 mm, or 20 mm to 32 mm. In some embodiments, the first or second end of the flexible cord can be secured to a prosthesis, or other device that substitutes for or supplements a missing or defective part of the body, e.g., a synthetic cardiac valve, or a porcine valve.

The flexible cord can be made of a variety of biocompatible polymeric materials or metallic materials that combine flexibility, high strength, and high fatigue resistance. For example, the flexible cord can be formed using materials including, but not limited to: polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane, stainless steel, titanium, a nickel-titanium alloy, a nickel-cobalt alloy, another cobalt alloy, tantalum, and combinations or mixtures thereof. In some embodiments, an antithrombotic component may be included in the chemical composition of a polymeric filament. In other embodiments, a flexible cord may be coated with a polymer that releases an anticoagulant and thereby reduces the risk of thrombus is formation. In other embodiments, additional therapeutic agents or combinations of agents may be used, e.g., antibiotics and anti-inflammatory agents. In some embodiments, the flexible cord can be maneuvered through a catheter.

The cross-sectional configuration of the flexible cord can be any suitable shape, such as round, oval, rectangular, square, etc. In some embodiments, the flexible cord may have a flattened cross-sectional shape, such as a "ribbon" shape. In other embodiments, the flexible cord may be a combination of shapes, such as for example, a flexible cord which is round on two sides with a flat surface on the opposing two sides. In some embodiments the entire flexible cord has the same shape, and in other embodiments, at least a portion of the flexible cord may have a different shape, e.g., a ribbon configuration, or at least a portion of the cord which is flattened, or has a flat surface. In some embodiments, the greatest outer diameter of the flexible cord may range from 0.1 mm to 0.6 mm, such as from 0.149 mm to 0.4 mm, or 0.15 mm to 0.2 mm. In some embodiments, the entire flexible cord has the same diameter. In other embodiments, at least a portion of the cord has a different diameter, e.g., a smaller diameter. In some embodiments, at least a portion of the cord may have both a different configuration and a different diameter, e.g., a portion of the cord may have a flat surface, where the portion of the cord having a flat surface has a largest outer diameter larger than the remainder of the cord. In some embodiments, the flexible cord does not comprise a knot.

A portion of the flexible cord between the first end and second ends is configured to be secured to tissue, such as cardiac tissue located below a cardiac valve leaflet. In some embodiments, a portion of the flexible cord between the first end and second ends can be secured to a prosthesis, or other device that substitutes for or supplements a missing or defective part of the body. The portion of the flexible cord between the first end and the second end that is configured to be secured to tissue can have the same shape and diameter as the remainder of the flexible cord, or in some embodiments it may have a different shape or diameter as the remainder of the flexible cord, as in the embodiments discussed above. For example, the portion of the cord between the first end and the second end that is configured to be attached to a second tissue may be flattened, or have a smaller or is larger diameter.

The portion of the flexible cord between the first end and the second end that is configured to be secured to tissue can further include a reinforcing member. A reinforcing member is an element which disperses the force of the securing flexible cord over a larger surface area. In some embodiments, the reinforcing member can be a pledget. Pledgets are generally buttressing or cushioning pads through which a suture or cord can be threaded, in order to prevent the suture strand or flexible cord from cutting into the tissue. A reinforcing member can be made of any suitable biologically compatible, needle pierceable resilient material sufficiently soft and flexible to effectively prevent damage to the tissue, e.g., papillary muscle. A reinforcing member is further made of material strong enough to resist pull-through by the flexible cord or suture to which it is mounted. The reinforcing member includes a top surface and a bottom surface, and can be configured in a variety of sizes and shapes, including rectangular, circular, elliptical, etc. For example, in certain embodiments the length of the reinforcing member may range from 1 mm to 10 mm, such as from 2 mm to 8 mm, or 3 mm to 4 mm. The width of the reinforcing member in some cases may range from 1 mm to 10 mm, such as from 2 mm to 8 mm, or 3 mm to 4 mm. In some embodiments, the thickness of the reinforcing member may range from 0.1 mm to 2 mm, such as from 0.2 mm to 0.5 mm, or 0.3 mm to 0.4 mm. The reinforcing elements may be fabricated of fabric, or felt, including polytetrafluoroethylene and polyester felt, polytetrafluoroethylene(PTFE), expanded PTFE, polyester and the like. In some embodiments, an antithrombotic component may be included in the chemical composition of the reinforcing member. In other embodiments, a reinforcing member may be coated with a polymer that releases an anticoagulant and thereby reduces the risk of thrombus formation. In other embodiments, additional therapeutic agents or combinations of agents may be used, e.g., antibiotics and anti-inflammatory agents.

In addition, the reinforcing element can have at least one opening wherein the flexible cord element may pass through. In other embodiments, the flexible cord is attached to the reinforcing element without passing through an opening, e.g., the flexible cord has been pulled through with a needle. In some embodiments, the is reinforcing element is mounted such that it is substantially fixed in a position on the flexible cord. For example, the reinforcing element can be sewn, or glued, or fused in any suitable manner so that it is fixed in position on the flexible cord, e.g., fixed in position halfway between the first and second ends of the flexible cord, such that the reinforcing element divides the flexible cord into two segments of equal length. In other embodiments, the reinforcing element is mounted such that it is slidably mounted on a flexible cord. By "slidably" is meant that the reinforcing element is attached to the flexible cord so that it is secure yet it is possible to move the reinforcing element along at least part of the length of the cord. For example, a flexible cord can have a reinforcing element (e.g., a pledget) initially positioned halfway between the first and second ends of the flexible cord. In using the synthetic chord device, it may be desirable to move the reinforcing element to a position closer to the first end before securing the reinforcing element to a tissue.

The synthetic chord devices further include attachment elements on both the first end and the second end of a flexible cord. The attachment elements are configured to attach a flexible cord, such as those described above, to a tissue, e.g., a cardiac valve leaflet. An attachment element is an element which includes a tissue piercing member and a securing member. The attachment element may be configured such that one or both of the tissue piercing members is attached to the securing member with a flexible member such as a suture. The attachment element may also be configured such that the tissue piercing member is directly attached to the securing member. One or both of the tissue piercing members may in some embodiments be releasably coupled to a securing member. In other embodiments, the attachment element may be configured such that one or both of the tissue piercing members is attached to a flexible member, such as a suture, which in turn is releasably coupled to the securing member. The coupling between the flexible member (and, thus, the tissue piercing member) and the securing member may be configured to actuate closure of the securing member upon release of the flexible member (or piercing member), as discussed below. For example, the coupling may hold a compression spring (which is positioned around a securing member) in a compressed state to brace the securing member open and releasably lock or is secure the securing member to the flexible member (or piercing member). In some embodiments, the attachment element can be secured to a prosthesis, or other device that substitutes for or supplements a missing or defective part of the body.

A flexible member as discussed above, such as a suture or a wire, can be formed from any suitable biocompatible material such as cotton, nylon, polyester, polypropylene, polyglycolic acid, polylactide, lactic acid, trimethlylene carbonate, polycaprolactone, or polydiaxanone or copolymers or homopolymers thereof, or a metal alloy, such as nitinol or stainless steel, a polymeric material, or any other suitable material and equivalents thereof. The material may be non-stretchable or stretchable, and have various cross-sectional diameters. In some embodiments, the flexible member does not comprise a knot. The flexible members may have a cross-sectional diameter of 0.003 inch, for example. The diameter and length of the flexible member will vary depending on the specific application. The flexible members, e.g., sutures, may be attached to the piercing members by crimping or swaging or otherwise attaching the piercing member or needle onto the flexible member, gluing the flexible member to the piercing member or needle, or any other suitable attachment method. Flexible members can also have various cross-sectional shapes, such as round, oval, etc.

A piercing member, or penetrating member is any device that can be used in a surgical, endovascular, or other interventional procedure that can be used to pierce through tissue, e.g., a needle. In some embodiments, the piercing member can also be used to pierce a prosthesis, e.g., synthetic valve. Piercing members that can be used in the subject devices include, but are not limited to, a conventional surgical needle, etc. The surgical needles useful in the devices of the present invention include conventional cardiac surgical needles and equivalents thereof. Suitable surgical needles can be manufactured from stainless steel, a stainless steel alloy, or any other suitable material, such as a polymeric material. The material can also have special coatings and sharpening methods that facilitate atraumatic tissue penetration. The shapes and sizes of the surgical needles can vary with the type and design of the needle. In some embodiments, the surgical needles have a curved or is arced shape. In some embodiments, the needles may be permanently "swaged" or attached to the suture material. In some embodiments, the suture may be designed to come off the suture with a sharp straight tug (e.g., "pop-offs").

Suitable lengths for the piercing members that are in the form of a needle can range in some embodiments from 4 mm to 70 mm, such as from 9 mm to 65 mm, or 20 mm to 40 mm. The diameter of the piercing member may range in certain embodiments from 0.05 mm to 0.6 mm, such as from 0.07 mm to 0.5 mm, or 0.1 mm to 0.4 mm. In some embodiments, the diameter of at least a portion of a piercing member is greater than the diameter of an attached flexible member or attached securing member, coupled so that the attached flexible member or attached securing member can easily be pulled through an opening formed in a tissue (or other material) by the piercing member, e.g., needle. The distal end or tip of the piercing member can be rigid to facilitate penetration of tissue. The remaining length of the piercing member can be rigid or flexible to facilitate movement of the piercing member through the tissue or other material. The tips can have various configurations and can, for example, have a piercing point, tapered point, or have a cutting or reverse cutting configuration for example, and have a shape such as conical, tapered, or grounded to attain a three or four facet tip. Piercing members can have any suitable shape or radius of curvature. Piercing members can have any suitable cross-sectional shape which may vary in different sections of the needle, e.g., round, rectangular, etc. In some embodiments, the piercing member can also be integrally formed with the flexible member (e.g., both piercing member and flexible member formed of the same material).

The attachment elements of the subject devices also include a securing member. A securing member is any device that can be used in a surgical, endovascular, or other interventional procedure that can be used to secure a flexible cord, or suture, e.g., an artificial mitral valve chorda tendinea. Suitable material for securing members can include shape memory materials, which are materials that have a temperature induced phase change, e.g., a material that if deformed when cool, returns to its "undeformed", or original, shape when warmed. Suitable material includes but is not limited to metals such as a nickel-titanium (NiTi) alloy (e.g., nitinol), a nickel-cobalt alloy, another cobalt alloy, alloys of CuZnAI, a thermoset plastic, stainless steel, a suitable biocompatible shape-memory material, a suitable biocompatible superelastic material, combinations thereof, and any suitable biocompatible shape memory alloy that can return to its undeformed, or original shape when warmed to body temperature, e.g., human body temperature. A securing member can have any suitable configuration. In some embodiments, for example, a securing member can have an anchor configuration, such that the arm segments of the anchoring members are constructed of a biocompatible material capable of being preset into an anchor shape. In another embodiment, a securing member can have a loop shape, such that the securing member is constructed of a biocompatible material capable of being preset into a loop shape. In some embodiments, a securing member can have an umbrella configuration, such that the arm segments of the anchoring members are constructed of a biocompatible material capable of being preset into an umbrella shape. The securing member may in other embodiments have various undeformed or deformed configurations such as a "parachute" configuration, an ellipse, a triangle, a square, a rectangle, spiral, conical, or other geometric shape, etc.

As discussed above, in some embodiments, the securing member may be releasably coupled to a tissue piercing member. In some embodiments, a flexible member, such as a suture, may be provided between at least one of the tissue piercing members and the securing member to facilitate threading the securing member.

In some embodiments, the securing member may secure the flexible cord without piercing the adjacent tissue, e.g., in the same manner as a surgical knot prevents a suture from pulling back through a tissue. In other embodiments, the securing member may secure the flexible cord by at least partially piercing the adjacent tissue. In some embodiments, the securing member may do both.

In some embodiments, the securing member is a self-closing fastener, which is any device that can be used in a surgical, endovascular, or other interventional procedure that can secure a flexible cord to tissue or other material (e.g., secure a flexible cord to a cardiac valve leaflet). In some embodiments, the self-closing is fasteners can be made of a shape memory material is meant a material that exhibits the shape memory effect, as discussed above. The shape memory alloy is preferably selected with a transformation temperature suitable for use with a stopped heart condition where cold cardioplegia has been injected for temporary paralysis of the heart tissue (e.g., temperatures as low as 8-10 degrees Celsius). The shape memory alloy may also be heat activated, or a combination of heat activation and pseudoelastic properties may be used. Self-closing fasteners that can be used in the subject devices include, but are not limited to, nitinol clips, such as the V60 U-clip Device™ (Medtronic Inc.) or any other preconfigured attachment device, etc.

A self-closing fastener can be held in an "open" configuration by a delivery mechanism that holds and retains the fastener in an open configuration. In some embodiments, a locking element can be included to connect the ends of the securing member when the securing member is in its closed position to prevent possible opening of the securing member over time. The locking element can in some embodiments be integrally formed with the securing member. In some embodiments, the self-closing fastener can include a release mechanism. Further details of self-closing fasteners that can be adapted for use with the present devices can be found in U.S. Pat. Nos. 6,913,607, 6,641,593, 6,613,059, 6,607,541, and 6,514,265.

As discussed above, a self-closing fastener can have any suitable configuration, including but not limited to an anchor configuration, a loop configuration, an "umbrella" or "parachute" configuration, an ellipse, a triangle, a square, a rectangle, spiral, conical, or other geometric shape, etc.

FIGS. 1A and B provide a view of the device in accordance with an embodiment of the invention. In FIG. 1A, the synthetic chord device of the subject invention is shown in an un-deployed state. The piercing member (e.g., a needle) is shown as element 110. The un-deployed self-closing fastener 130 is attached to the needle by flexible member (e.g., suture) 120. Flexible cord 140 is shown with a reinforcing member 150 (e.g., a pledget).

Figure 1B:
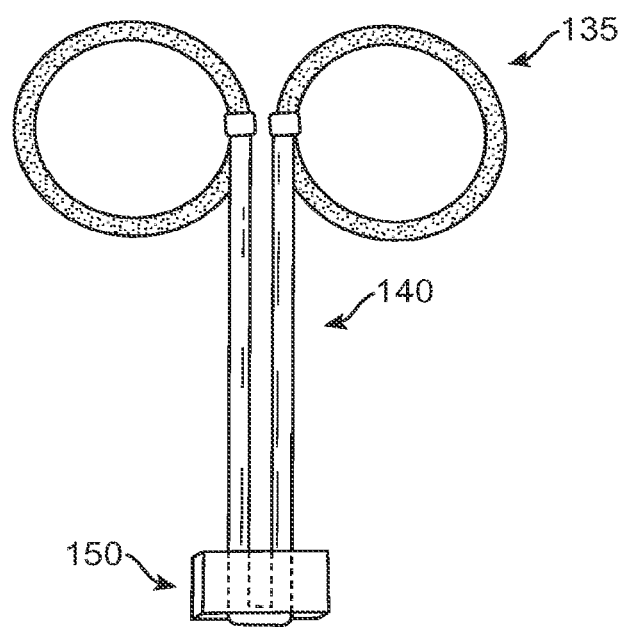

In FIG. 1B, the synthetic chord device of the subject invention is shown in a deployed state. The needle has been removed, and the self-closing fastener has is been deployed, shown as element 135.

Figure 5A:
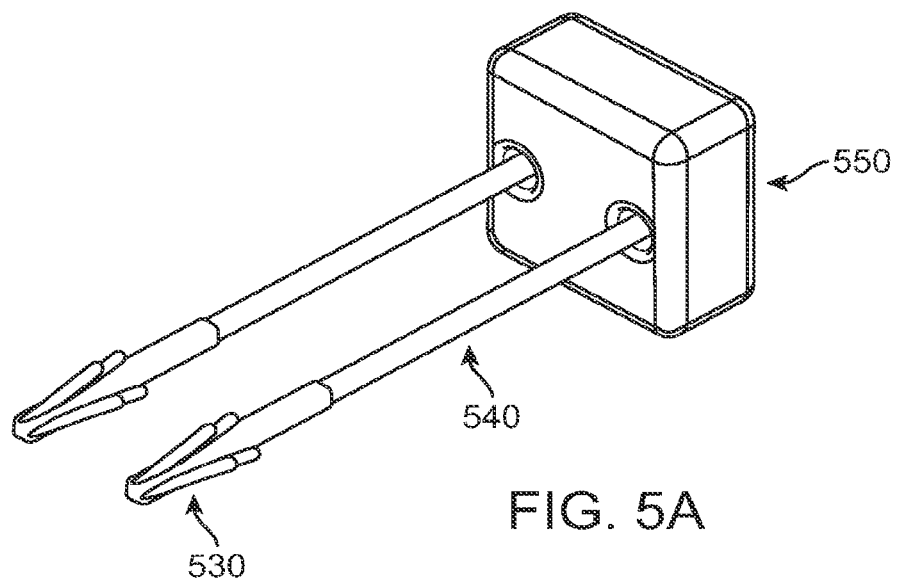
FIGS. 5A and 5B provide another view of the device in accordance with an embodiment of the invention.

FIGS. 5A and B provide a view of the device in accordance with another embodiment of the invention, in which the self-closing fastener has an "umbrella" configuration. In FIG. 5A, the synthetic chord device of the subject invention is shown in an un-deployed state. The un-deployed self-closing fastener 530 is attached to a needle by flexible member (not shown). Flexible cord 540 is shown with reinforcing member 550.

Figure 5B:
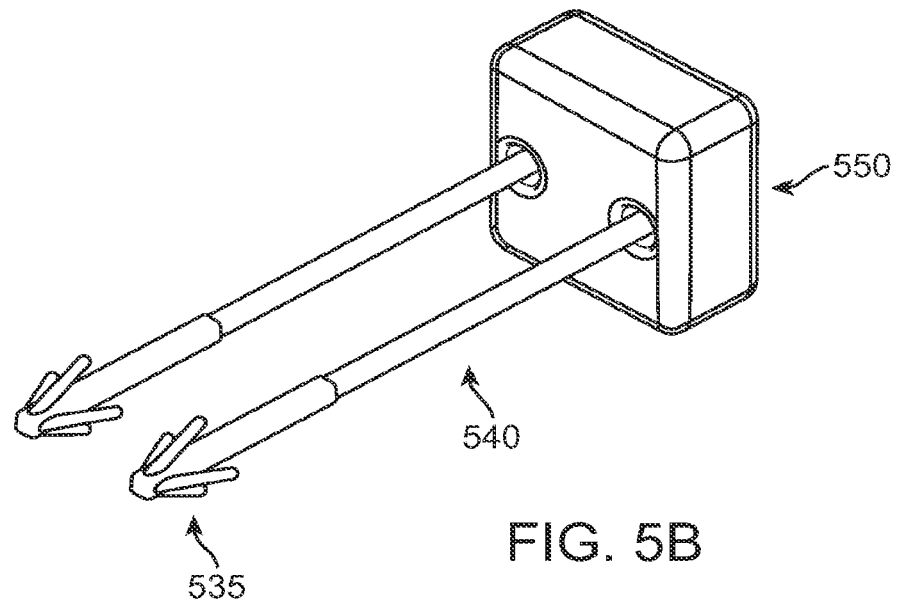

In FIG. 5B, the synthetic chord device of the subject invention is shown in a deployed state. The self-closing fastener has been deployed, shown as element 535.

Methods

The subject devices find use in methods for fastening a tissue, such as a cardiac valve leaflet, to a second tissue, such as a papillary muscle, with a flexible cord (e.g., a synthetic mitral valve chorda tendinea). The subject devices therefore find use in methods in which a prolapsed cardiac valve leaflet, such as a mitral valve leaflet, is repaired. The subject devices can be used in an open surgical procedure, a minimally invasive surgical procedure, an endovascular procedure, or other interventional procedure.

Methods for repair of a cardiac valve, such as a mitral valve, are discussed below. When performing a conventional heart valve repair procedure, the surgeon makes incisions into the thoracic cavity and pericardium, and then into aorta or myocardium in order to have access to the damaged heart valve. The procedure may be an open procedure in which the sternum is opened and the ribs are spread with a conventional retractor, or a minimally invasive procedure wherein the heart and heart valve are accessed through minimally invasive openings in the thoracic cavity, such as through trocar cannulas or small incisions in the intercostal spaces. The heart may also be accessed through the lumen of an artery. The minimally invasive procedures can be viewed remotely using a camera and monitor, or in is some cases directly.

Figure 2:
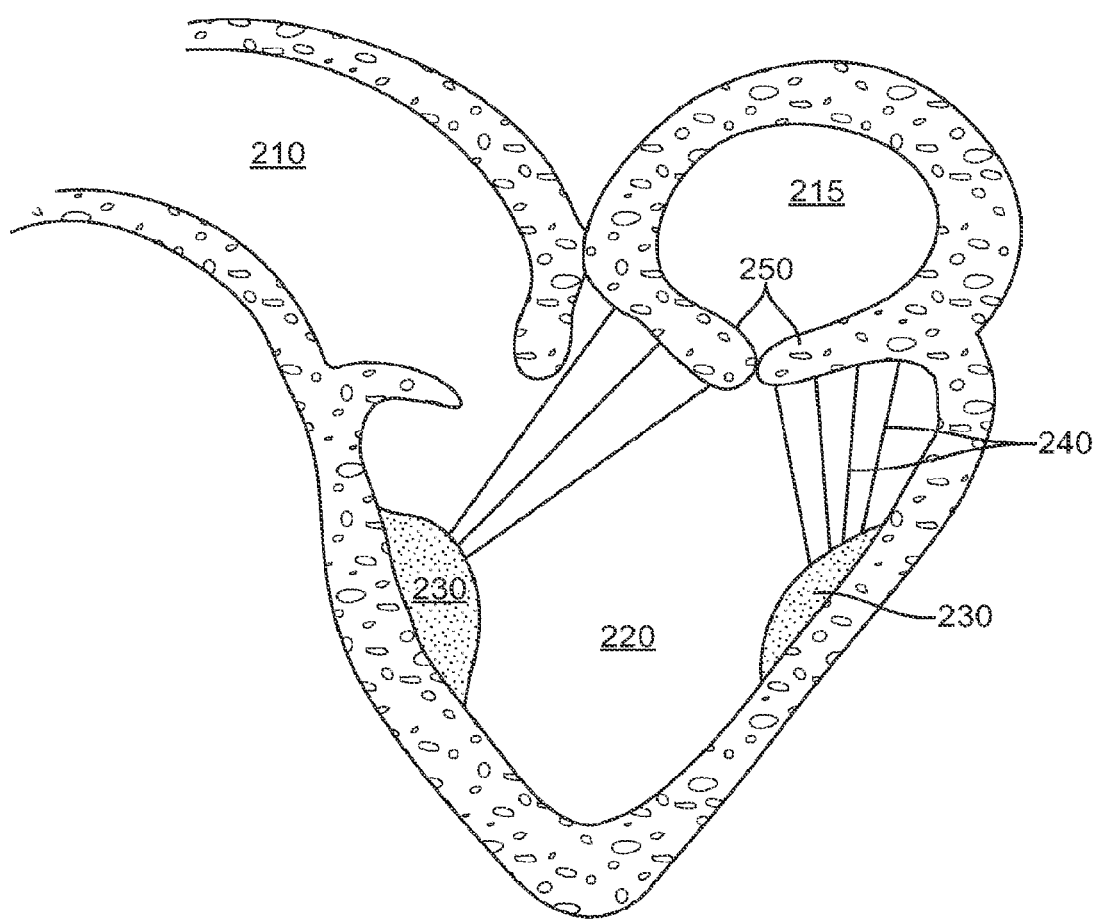
FIG. 2 provides a schematic view of the normal left side of the heart.

FIG. 2 depicts a schematic drawing of the left side of the heart. The aortic arch 210, left atrium 215, and left ventricle 220 are shown, with the mitral valve 250 located between the left ventricle and the left atrium. The chordae tendineae are shown as elements 240, attached to the leaflets of the mitral valve on one end, and the papillary muscle 230 in the left ventricle on the other end.

After exposure of the mitral valve and the subvalvular area, the desired length of the neochord, or flexible cord, is determined by measuring the distance between the prolapsed leaflet and the cardiac tissue located below the prolapsed mitral valve leaflet using methods that are well known in the art. The desired length for the flexible cord can be determined using any suitable measuring device, such as a caliper, or a Mohr Suture Ruler Device™ (Geister, Tuttlingen, Germany). For example, a caliper or sterile disposable flexible tape measure can be used to assess the correct length for the synthetic mitral valve chordae by measuring the distance between the tip of the papillary muscle and the edge of a non-prolapsing segment of the mitral valve leaflet. The measurement can also be confirmed by comparison with pre-operative transesophageal echocardiography (TEE).

Figure 3:
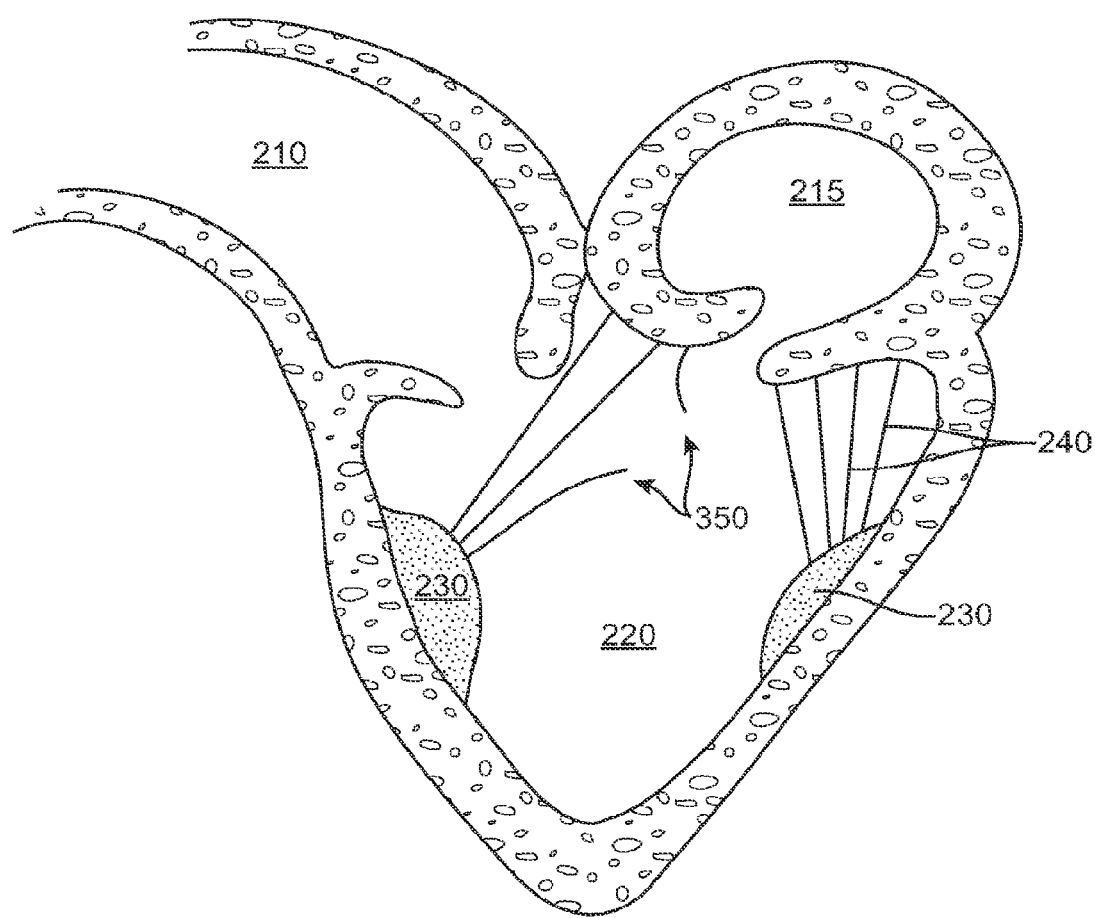
FIG. 3 provides a schematic view of the left side of the heart demonstrating a ruptured chorda tendinea of the mitral valve.

An illustration of a rupture, or breakage of one of the chorda tendinea which can be repaired using the methods and devices of the subject invention is shown in FIG. 3. The ruptured, or broken chorda tendinea is shown as element 350. The leaflets of the mitral valve now no longer coapt, or close, and during systole, blood can flow from the left ventricle back into the left atrium, i.e., mitral regurgitation.

The synthetic chord device having a flexible cord with the desired length, or the closest to the desired length, is then selected from among a set of synthetic chord devices. The set of synthetic chord devices can include two or more flexible cords of the same or of different lengths, such as three cords, or four cords, etc.

The piercing member on the first end, e.g., a needle, is first advanced through the cardiac tissue below the prolapsed mitral valve leaflet, e.g., a papillary muscle, and pulled through until the reinforcing element, e.g., a pledget, is in substantial contact with a surface of the papillary muscle. The needle is then advanced through the leaflet of the prolapsed mitral valve until the securing member, e.g., a self-closing fastener such as a nitinol clip, has passed through the leaflet.

The position of the prolapsed valve leaflet may be adjusted by coordinating the tension of the cord and the location of the leaflet. For example, a practitioner (e.g., a doctor, surgeon, technician, etc.) may move the prolapsed valve into a correct (e.g., non-prolapsed) position by adjusting the position of the valve leaflet directly by pushing against the anchor attached to the valve leaflet (e.g., using the fastener to push against the anchor and applying tension to the cord). The valve leaflet position may be adjusted in real-time in a beating heart (e.g., using echocardiography). For example, the valve leaflet may be repositioned while monitoring mitral regurgitation (MR). Once any MR is reduced or eliminated, the valve leaflet is in the correct position.

Once the valve leaflet is positioned correctly, the attachment member can then be deployed (e.g., the self-closing fastener deploys, or closes, for example, as shown in FIGS. 1B and 5B). The piercing member on the second end, e.g., a needle, is then advanced through the papillary muscle below the prolapsed mitral valve leaflet, thereby securing the pledget against the papillary muscle. The second tissue piercing member, e.g., needle, is then advanced through the same prolapsed mitral valve leaflet, until the second securing member has passed through the leaflet. The second attachment element is then deployed, as discussed above. It should be noted that the number of synthetic chord devices required to secure the connecting tissues together may vary depending on the procedure and the anatomy.

Figure 4A:
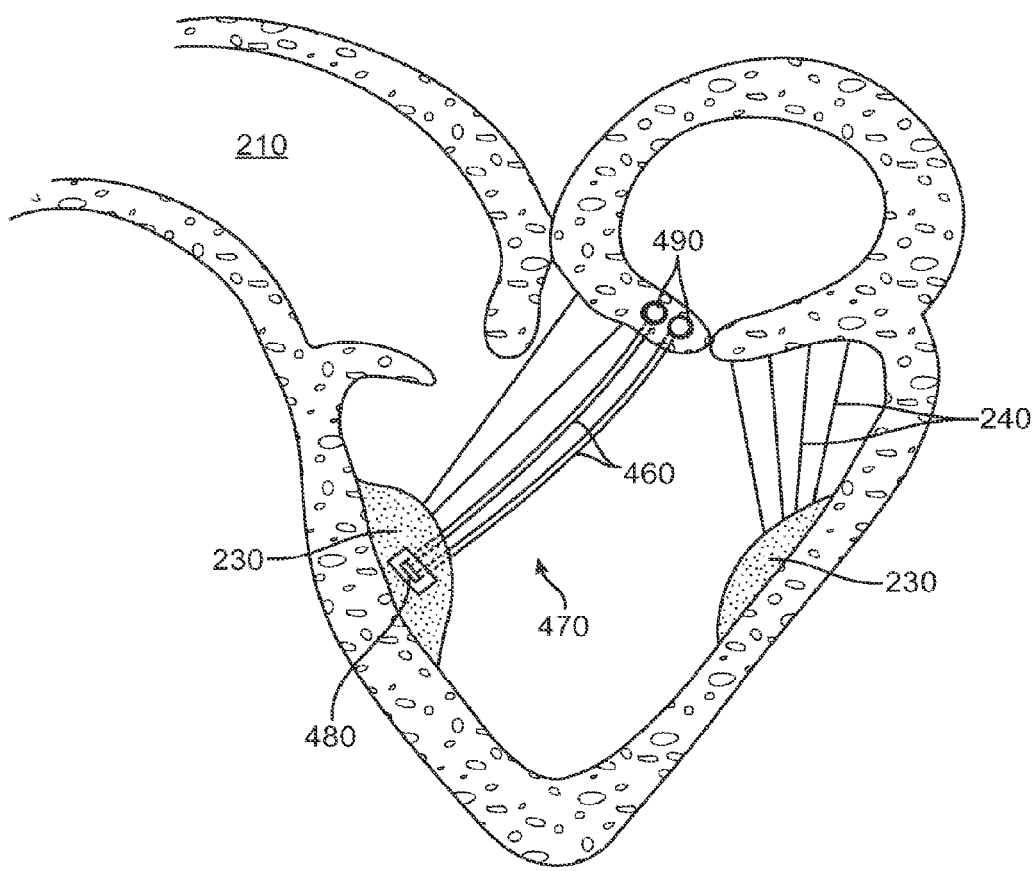
FIGS. 4A and B provide a schematic view of the left side of the heart after repair of the ruptured chorda tendinea of the mitral valve with embodiments of the synthetic chord device of the subject invention.

FIG. 4A shows an embodiment of a repair of the ruptured chorda tendinea with a synthetic chord device 470 of the subject invention. The flexible cord 460 is attached to the mitral valve leaflet at both ends with securing members 490, which in this embodiment have a ring shape. Flexible cord 460 is shown secured to the tissue below the mitral valve leaflet (e.g., the papillary muscle) with reinforcing member 480. After repair, the leaflets of the mitral valve 250 now coapt, or close, and blood can no longer flow from the left ventricle back into the left atrium during systole.

Figure 4B:
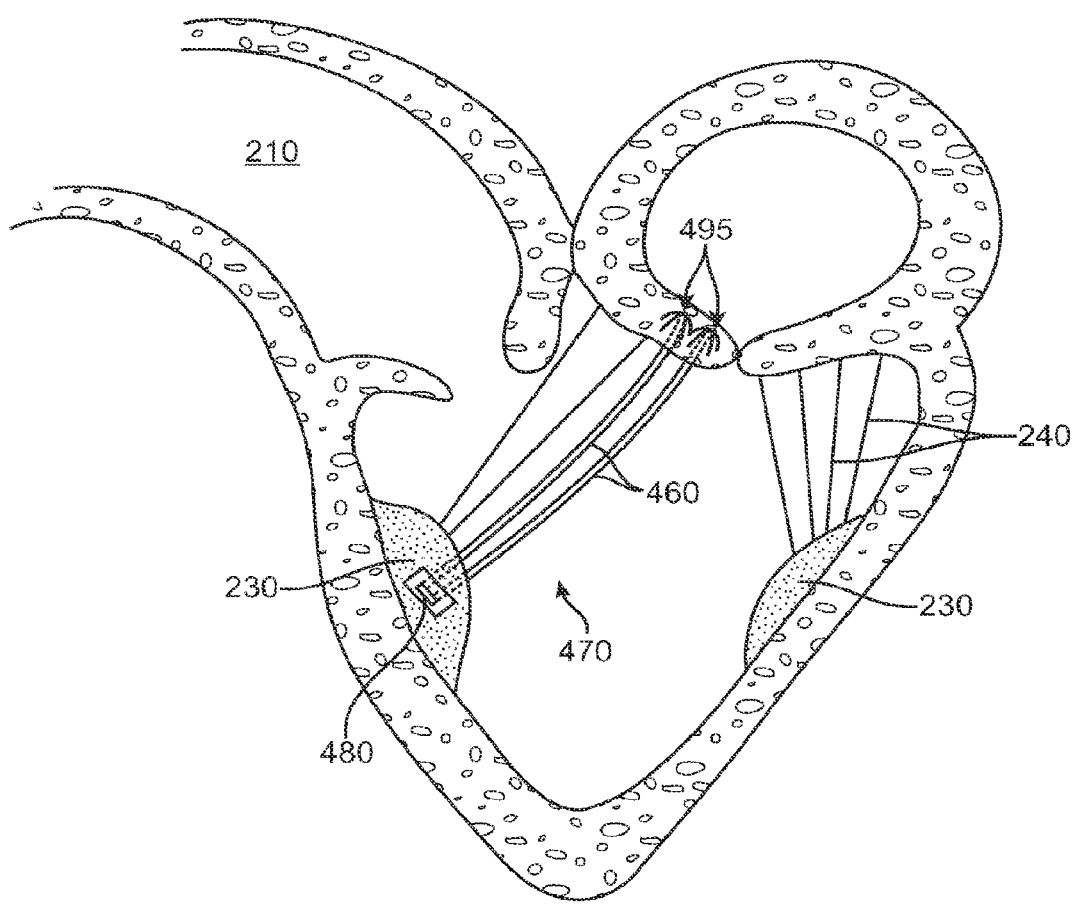

FIG. 4B shows another embodiment of a repair of the ruptured chorda tendinea with a synthetic chord device 470 of the subject invention. The flexible is cord 460 is attached to the mitral valve leaflet at both ends with securing members 495, which in this embodiment have a four-pronged "umbrella" shape, similar to the embodiment shown in FIGS. 5A and B. In this embodiment, the surface area of the mitral valve leaflet which is contacted by the securing member is increased. Flexible cord 460 is again shown secured to the tissue below the mitral valve leaflet (e.g., the papillary muscle) with reinforcing member 480.

Figure 6:
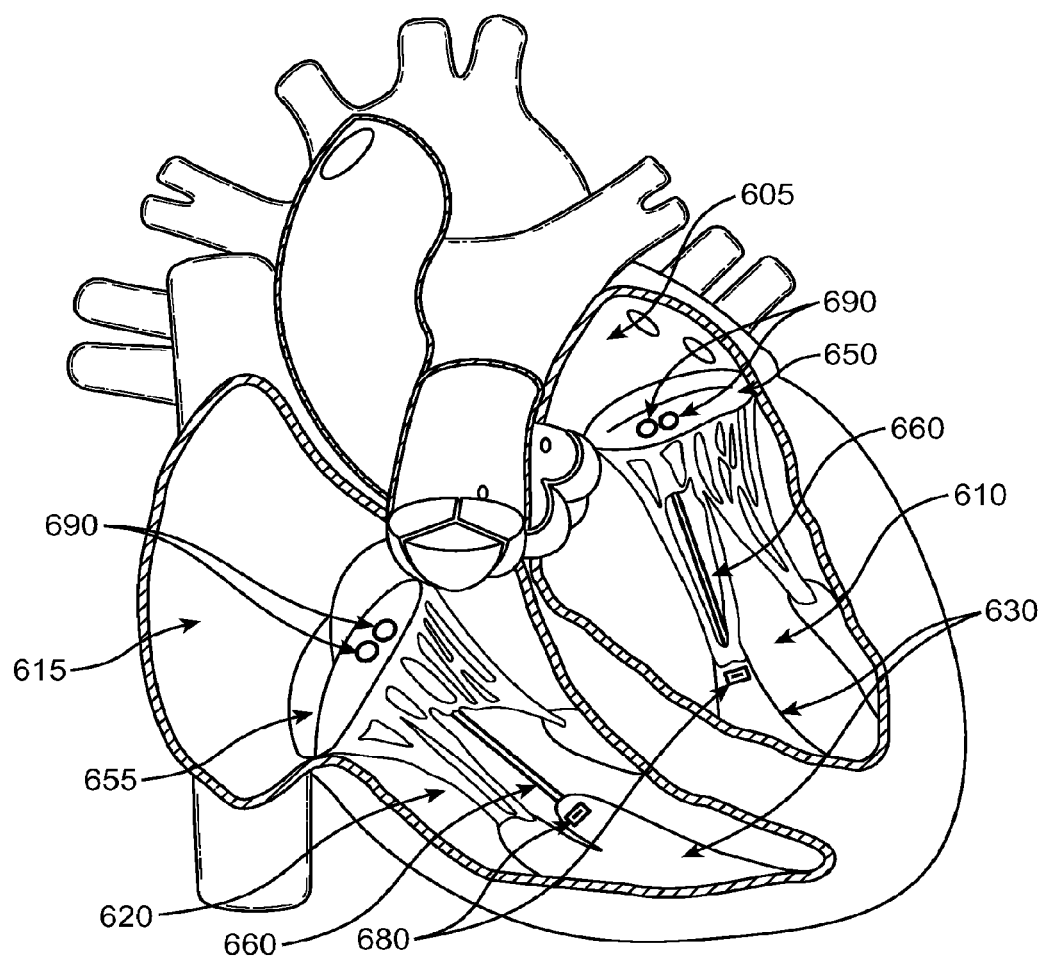
FIG. 6 provides a schematic view of the heart after repair of both the ruptured chordae tendineae of the mitral valve and tricuspid valves with embodiments of the synthetic chord device of the subject invention.

FIG. 6 shows an embodiment of a repair of ruptured chordae tendineae of both the mitral and tricuspid valves with synthetic chord devices of the subject invention. In this view, the left atrium is shown as element 605, the left ventricle is element 610; the right atrium is element 615, and the right ventricle is shown as element 620. The flexible cords 660 are attached to the mitral valve 650 or tricuspid valve 655 leaflet at both ends with securing members 690. Flexible cord 660 is shown secured to the tissue below the valve leaflets (e.g., papillary muscle, 630) with reinforcing members 680. After repair, the leaflets of the mitral valve 650 and tricuspid valve 655 now coapt, or close, and blood can no longer flow from the ventricles back into the atria during systole.

By this method, a prolapsed mitral valve leaflet can be repaired by securing the leaflet to the papillary muscle below. Using the methods and devices of the subject invention, a mitral valve repair procedure can be successfully completed without the need for the time-consuming step of cutting the desired length of synthetic cord while the patient is on the operating table, thereby decreasing the amount of time needed to place a patient on cardio-pulmonary bypass. In addition, the subject methods and devices obviate the need for tying sutures and ensuring that the suture material does not become tangled, difficulties which are exacerbated by the small size of the tissues involved and the often limited field of the operation.

Any appropriate prolapsed valve leaflet may be treated as described herein, including mitral valve leaflets and tricuspid valve leaflets. Further, these methods may be performed using one or more catheters or using non-catheter surgical methods, or using a combination of catheter-type surgical methods and non-catheter type surgical methods. The methods of the subject invention may also be used in is combination with other surgical procedures, e.g. replacement of a mitral valve annulus, etc.

In some variations, the flexible cord may be advanced via one or more catheters to the proximity of the prolapsed valve leaflet in an anterograde approach (e.g., from above the mitral valve). Alternatively, the flexible cord may be advanced via a retrograde approach (e.g., from below the mitral valve). In all of the methods described herein, the cardiac tissue located below the prolapsed valve (to which one of the anchors is secured) may be selected from the group consisting of a papillary muscle and a ventricular wall.

The subject methods also include the step of diagnosing a patient in need of cardiac valve repair, e.g., mitral valve repair. Primary mitral regurgitation is due to any disease process that affects the mitral valve device itself. The causes of primary mitral regurgitation include myxomatous degeneration of the mitral valve, infective endocarditis, collagen vascular diseases (ie: SLE, Marfan's syndrome), rheumatic heart disease, ischemic heart disease/coronary artery disease, trauma, balloon valvulotomy of the mitral valve, certain drugs (e.g. fenfluramine). If valve leaflets are prevented from fully coapting (i.e., closing) when the valve is closed, the valve leaflets will prolapse into the left atrium, which allows blood to flow from the left ventricle back into the left atrium, thereby causing mitral regurgitation.

The signs and symptoms associated with mitral regurgitation can include symptoms of decompensated congestive heart failure (ie: shortness of breath, pulmonary edema, orthopnea, paroxysmal nocturnal dyspnea), as well as symptoms of low cardiac output (i.e., decreased exercise tolerance). Cardiovascular collapse with shock (cardiogenic shock) may be seen in individuals with acute mitral regurgitation due to papillary muscle rupture or rupture of a chorda tendinea. Individuals with chronic compensated mitral regurgitation may be asymptomatic, with a normal exercise tolerance and no evidence of heart failure. These individuals however may be sensitive to small shifts in their intravascular volume status, and are prone to develop volume overload (congestive heart failure).

Findings on clinical examination depend of the severity and duration of mitral regurgitation. The mitral component of the first heart sound is usually soft and is is followed by a pansystolic murmur which is high pitched and may radiate to the axilla. Patients may also have a third heart sound. Patients with mitral valve prolapse often have a mid-to-late systolic click and a late systolic murmur.

Diagnostic tests include an electrocardiogram (EKG), which may show evidence of left atrial enlargement and left ventricular hypertrophy. Atrial fibrillation may also be noted on the EKG in individuals with chronic mitral regurgitation. The quantification of mitral regurgitation usually employs imaging studies such as echocardiography or magnetic resonance angiography of the heart. The chest x-ray in patients with chronic mitral regurgitation is characterized by enlargement of the left atrium and the left ventricle. The pulmonary vascular markings are typically normal, since pulmonary venous pressures are usually not significantly elevated. An echocardiogram, or ultrasound, is commonly used to confirm the diagnosis of mitral regurgitation. Color doppler flow on the transthoracic echocardiogram (TTE) will reveal a jet of blood flowing from the left ventricle into the left atrium during ventricular systole. Because of the difficulty in getting accurate images of the left atrium and the pulmonary veins on the transthoracic echocardiogram, a transesophageal echocardiogram (TEE) may be necessary to determine the severity of the mitral regurgitation in some cases. The severity of mitral regurgitation can be quantified by the percentage of the left ventricular stroke volume that regurgitates into the left atrium (the regurgitant fraction). Other methods that can be used to assess the regurgitant fraction in mitral regurgitation include cardiac catheterization, fast CT scan, and cardiac MRI.

Indications for surgery for chronic mitral regurgitation include signs of left ventricular dysfunction. These include an ejection fraction of less than 60 percent and a left ventricular end systolic dimension (LVESD) of greater than 45 mm.

The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

Kits

Also provided are kits that at least include the subject devices. The subject kits at least include a synthetic chord device of the subject invention and instructions for how to use the synthetic chord device in a procedure.

In some embodiments, the kits can include a set of two or more synthetic chord devices. In other embodiments, a set of synthetic chord devices can include at least three synthetic chord devices, e.g., four or more, five or more, six or more, etc.

In some embodiments, a set of synthetic chord devices includes two or more synthetic chord devices in which at least two of the synthetic chord devices have flexible cords of different lengths. In other embodiments, the flexible cord portions of the synthetic chord devices are all of differing lengths. In some embodiments, a set of synthetic chord devices can have two or more synthetic chord devices in which the flexible cords are of the same length. A set of synthetic chord devices can therefore have two or more some synthetic chord devices in which some are of the same length, and some are of a different length. For example, in one embodiment a set of six synthetic chord devices can have two synthetic chord devices in which the flexible cord portion is 16 mm in length, which can provide two segments with a length of 8 mm; two synthetic chord devices in which the flexible cord portion is 20 mm in length, which can provide two segments with a length of 10 mm; and two synthetic chord devices in which the flexible cord portion is 24 mm in length, which can provide two segments with a length of 12 mm. In another embodiment, a set of synthetic chord devices can have four synthetic chord devices in which the flexible cord portion in all of them is 20 mm in length, such that each flexible cord portion can provide two segments with a length of 10 mm.

In addition, in some embodiments, the synthetic chord devices can be color-coded, such that a desired length of the synthetic mitral valve chord, or flexible cord element, can be easily determined. For example, a package with multiple synthetic is chord devices can have sutures of two different colors arranged in an alternating pattern to allow a medical practitioner (e.g., scrub nurse) to readily distinguish one synthetic chord device from another. For example, a set of ten synthetic chord devices in a kit can be arranged in two horizontal rows of five in each row. An exemplary arrangement of associated suture colors would be, in the top row: white, green, white, green, white, and in the bottom row: green, white, green, white, green. (further details of packaging that can be adapted for use with the synthetic chord devices of the subject invention are disclosed in U.S. Pat. No. 6,029,806, incorporated herein by reference). In this manner, a scrub nurse can readily associate each pair of tissue-piercing members (e.g., needles) with the synthetic chord device containing the correct length of synthetic mitral valve chord, or flexible cord. By color coding the synthetic chord devices with alternating, contrasting suture colors, more synthetic chord devices can be stored in a package of a given size without causing confusion. The two needles associated with each synthetic chord device can be sufficiently separated to allow grasping of each needle with a needle holder, while maintaining identification of the pair of needles as belonging to the same synthetic chord device.

The kit can also include a measuring tool, which can be disposable, for determining a desired length of a synthetic chord by measuring a desired distance, such as the distance between a prolapsed cardiac valve leaflet and cardiac tissue located below the prolapsed cardiac valve leaflet, including but not limited to any suitable measuring device, such as a caliper, a Mohr Suture Ruler Device™ (Geister, Tuttlingen, Germany), or sterile disposable flexible tape measure.

The instructions for using the devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g., CD-ROM, diskette, etc. The instructions may take any form, including complete instructions for how to is use the device or as a website address with which instructions posted on the world wide web may be accessed.

The following example is offered by way of illustration and not by way of limitation.

EXPERIMENTAL

A patient is prepared for a mitral valve prolapse repair procedure in a conventional manner. The patient is anesthetized using conventional anesthesia and anesthesiology procedures.

The patient undergoes an intraoperative transesophageal echocardiography to determine the mechanism of the mitral regurgitation (MR), and to estimate the required length for the synthetic mitral valve neochordae. The intraoperative transesophageal echocardiography also serves as a baseline evaluation for assessing the quality of the repair, and for follow-up evaluation.

The patient's skin overlying the sternum and surrounding areas is swabbed with a conventional disinfecting solution. Next, the surgeon accesses the patient's thoracic cavity via a right anterolateral mini-thoracotomy, through a 3 cm incision. Three additional small 10 mm ports are made for video camera, a left atrial retractor, and a transthoracic aortic clamp.

The heart is then accessed by opening the pericardium. Next, the patient is placed on cardiopulmonary bypass in a conventional manner and the patient's heart is stopped from beating in a conventional manner. The surgeon then performs the mitral valve repair in the following manner: The valve is accessed through an incision in the left atrium or across the atrial septum if bi-caval cannulation is utilized for cardiopulmonary bypass. After exposure of the mitral valve and the subvalvular area, the desired length of the neochord, or flexible cord, is determined by measuring the distance between the tip of the papillary muscle and the edge of a non-prolapsing segment of the mitral valve leaflet.

A synthetic chord device as depicted in FIG. 1 is selected from a set of synthetic chord devices of the present invention based on the measurement. The needle on the first end is advanced through the papillary muscle located below the mitral valve leaflet, and pulled through until the pledget is in substantial contact with a surface of the papillary muscle. The needle is then advanced through the leaflet of the prolapsed mitral valve until the un-deployed Nitinol U-clip has passed through the leaflet.

Once the length of the synthetic mitral valve chord and the function of the mitral valve has been assessed, the Nitinol U-clip is deployed. The needle on the second end is advanced through the papillary muscle below the prolapsed mitral valve leaflet, adjacent to the site of the first end of the flexible cord, thereby securing the pledget against the papillary muscle. The second needle with the un-deployed Nitinol U-clip is then advanced through the same prolapsed mitral valve leaflet until the Nitinol U-clip has been pulled through the leaflet.

Once the length of the synthetic mitral valve chord and the function of the mitral valve has been assessed, the second Nitinol U-clip is deployed.

Post-repair valve competency can be assessed by filling and pressurizing the left ventricle with saline and observing the valve. The incisions are then closed and the patient weaned, or removed, from cardiopulmonary bypass. After weaning the patient from cardiopulmonary bypass, valve function is examined with transesophageal echocardiography or like means. The chest and skin incisions are then closed to complete the procedure.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for connecting a first tissue to a second tissue, the method comprising:
   (a) providing a synthetic chord device comprising:
      (i) a flexible cord;
      (ii) an attachment element comprising a tissue piercing member and a securing member separated from each other by a flexible member, wherein the tissue piercing member is a needle and the securing member is a self-closing fastener comprising a shape memory material; and
      (iii) a reinforcing element that is a pledget;
   (b) passing the tissue piercing member through the second tissue in a manner sufficient to contact to the reinforcing element to the second tissue;
   (c) passing the tissue piercing member through the first tissue; and
   (d) deploying the securing element to connect the first tissue to the second tissue.

2. The method according to claim 1, further comprising:
   (a) determining a desired length of the flexible cord by measuring a desired distance between the first tissue and the second tissue; and
   (b) selecting a synthetic chord device having a flexible cord with the desired length from a set of two or more synthetic chord devices.

3. The method according to claim 1, wherein the shape memory material comprises a nickel alloy.

4. The method according to claim 3, wherein the nickel alloy comprises a nickel-titanium alloy.

5. The method according to claim 3, wherein the nickel alloy comprises a nickel-cobalt alloy.

6. The method according to claim 1, wherein the flexible cord comprises expanded PTFE.

7. The method according to claim 1, wherein said flexible cord has a length ranging from 8 mm to 60 mm.

8. The method according to claim 1, wherein the first tissue is a cardiac valve leaflet and the second tissue is a papillary muscle.

* * * * *